US011266318B2

(12) United States Patent
Deno

(10) Patent No.: US 11,266,318 B2
(45) Date of Patent: Mar. 8, 2022

(54) BLOOD PRESSURE MONITOR, ASSESSMENT SYSTEM, AND METHOD OF CONTROLLING BLOOD PRESSURE MONITOR FOR ASSESSING AUTONOMIC NERVE FUNCTION OF A SUBJECT

(71) Applicants: OMRON HEALTHCARE CO., LTD., Muko (JP); OMRON CORPORATION, Kyoto (JP)

(72) Inventor: Toru Deno, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 29 days.

(21) Appl. No.: 16/568,651

(22) Filed: Sep. 12, 2019

(65) Prior Publication Data

US 2020/0000343 A1    Jan. 2, 2020

Related U.S. Application Data

(63) Continuation of application No. PCT/JP2017/045460, filed on Dec. 19, 2017.

(30) Foreign Application Priority Data

Mar. 14, 2017    (JP) .............................. JP2017-048594

(51) Int. Cl.
*A61B 5/022*    (2006.01)
*A61B 5/021*    (2006.01)
*A61B 5/00*    (2006.01)

(52) U.S. Cl.
CPC .......... *A61B 5/022* (2013.01); *A61B 5/02116* (2013.01); *A61B 5/6824* (2013.01);
(Continued)

(58) Field of Classification Search
CPC combination set(s) only.
See application file for complete search history.

(56) References Cited

U.S. PATENT DOCUMENTS 3,585,987 A *  6/1971  Svensson ............... A61B 5/352
                                                   600/485
5,522,395 A *  6/1996  Shirasaki ........... A61B 5/02116
                                                   600/494
(Continued)

FOREIGN PATENT DOCUMENTS

CN      102176860 A     9/2011
JP      2006-102265 A   4/2006
(Continued)

OTHER PUBLICATIONS

Espacenet Translation of JP-2016195656-A retrieved on Mar. 23, 2021 (Year: 2016).*

(Continued)

*Primary Examiner* — Etsub D Berhanu
*Assistant Examiner* — Robert T Pazhwak
(74) *Attorney, Agent, or Firm* — Oliff PLC

(57)    ABSTRACT

A blood pressure monitor includes a processor configured to control a cuff pressure and calculate blood pressure information of a subject based on a cuff pressure signal representing the cuff pressure and a pulse wave signal superimposed on the cuff pressure signal. The processor calculates first blood pressure information of the subject who has maintained a recumbent position for a prescribed time period, maintains the cuff pressure at a first pressure lower by a prescribed value than a systolic blood pressure included in the first blood pressure information, determines if an amplitude of the pulse wave signal is equal to or greater than a threshold value when the cuff pressure is maintained at the first pressure and the subject is in an upright position, (Continued)

assesses an autonomic nerve function of the subject based on a result of the determination, and outputs a result of the assessment.

14 Claims, 7 Drawing Sheets

(52) U.S. Cl.
CPC ......... *A61B 5/0022* (2013.01); *A61B 5/02141* (2013.01); *A61B 5/742* (2013.01)

(56) References Cited

U.S. PATENT DOCUMENTS

| 8,382,679 B2* | 2/2013 | Ono | A61B 5/4035 |
| | | | 600/554 |
| 2016/0029904 A1* | 2/2016 | Quinn | A61B 5/0024 |
| | | | 600/499 |

FOREIGN PATENT DOCUMENTS

| JP | 3976278 B1 | 9/2007 |
| JP | 2008-99876 A | 5/2008 |
| JP | 2012-508056 A | 4/2012 |
| JP | 5944550 B1 | 7/2016 |
| JP | 2016-195656 A | 11/2016 |
| WO | 2010/053446 A1 | 5/2010 |

OTHER PUBLICATIONS

Winker et al., "Schellong test in orthostatic dysregulation: a comparison with tilt-table testing", 2005, The Mddle European Jounral of Medicine, DOI 1171-2: 36-41; pp. 1-2 (Year: 2005).*

Hamunen et al.; "Effect of pain on autonomic nervous system indicies derived from photoplethysmography in healthy volunteers"; Feb. 26, 2012; British Journal of Anasthesia' 108 (5): 838-44; pp. 1-2 (Year: 2012).*

Mar. 13, 2018 International Search Report issued in International Patent Application No. PCT/JP2017/045460.

Aug. 11, 2021 Office Action issued in Chinese Patent Application No. 201780088313.9.

Kobayashi, "Orthostatic Regulatory Disorder (OD)", Illustrated Family Medicine Classic, Jan. 31, 2002, pp. 232-235, Wenhui32 Press.

Hanping Jiang, "Athletes' Erectile Adjustment Disorder", Sport Diseases, Jun. 30, 2011, pp. 142-149, Hunan Science and Technology Press.

* cited by examiner

BLOOD PRESSURE MONITOR, ASSESSMENT SYSTEM, AND METHOD OF CONTROLLING BLOOD PRESSURE MONITOR FOR ASSESSING AUTONOMIC NERVE FUNCTION OF A SUBJECT

The present application is a continuation of International application No. PCT/JP2017/045460, filed Dec. 19, 2017, which claims priority to Japanese Patent Application No. 2017-048594, filed Mar. 14, 2017, the entire contents of each of which are incorporated herein by reference.

BACKGROUND

The present disclosure relates to a blood pressure monitor, an assessment system, and a method of controlling a blood pressure monitor, and particularly to a blood pressure monitor for assessing an autonomic nerve function of a subject, an assessment system, and a method of controlling a blood pressure monitor.

Autonomic nerves include sympathetic nerves which function when one is mainly in an active state and parasympathetic nerves which function when one is mainly in a resting state. When the autonomic nerve function is normal, switching between a sympathetic nerve dominant state and a parasympathetic nerve dominant state is made while the sympathetic nerves and the parasympathetic nerves are balanced. When the autonomic nerve function is not normal, however, balance of the autonomic nerves is lost and various symptoms such as dizziness and lightheadedness are caused. Various techniques for diagnosis of such an autonomic nerve function have been proposed.

For example, Japanese Patent Laying-Open No. 2016-195656 (PTL 1) discloses an autonomic nerve function diagnosis apparatus. The apparatus includes heart rate measuring means for measuring a heart rate of a subject, display means for displaying biological information, instruction means for instructing the subject to perform a stand-up action, and control means for determining whether or not the autonomic nerve function of the subject is abnormal based on whether or not increase in heart rate representing a difference in heart rate between before and after the instruction of the stand-up action given by the instruction means is within a normal range set in advance and controlling the display means to show a result of determination.

SUMMARY

When one stands up from a lying position, blood is pooled in lower body by gravity and a blood pressure is lowered. At this time, sympathetic nerves function to prevent lowering in blood pressure so that blood vessels in the lower body constrict to maintain the blood pressure. Parasympathetic nerve activities are reduced to increase cardiac output and maintain the blood pressure. When one suffers from orthostatic dysregulation representing dysautonomia, this compensatory mechanism fails due to disorder of the autonomic nerves, a blood pressure does not quickly rise, and such syndromes as dizziness and lightheadedness are caused.

Though PTL 1 discloses determination as to whether or not the autonomic nerve function of a subject is abnormal based on whether or not a difference in heart rate between before and after the stand-up action is within a normal range set in advance, it fails to disclose an approach to assessment of the autonomic nerve function based on a blood pressure value.

In one aspect, an object of the present disclosure is to provide a blood pressure monitor capable of more accurately assessing an autonomic nerve function of a subject, an assessment system, and a method of controlling a blood pressure monitor.

A blood pressure monitor according to one embodiment includes a processor configured to: control a cuff pressure representing an internal pressure of a cuff attached to a measurement site of a subject; and calculate blood pressure information of the subject based on a cuff pressure signal representing the cuff pressure and a pulse wave signal superimposed on the cuff pressure signal. The calculation includes calculating first blood pressure information of the subject who has maintained a recumbent position for a prescribed time period. The processor is configured to: maintain the cuff pressure at a first pressure lower by a prescribed value than a systolic blood pressure included in the first blood pressure information; determine whether or not an amplitude of the pulse wave signal of the subject is equal to or greater than a threshold value when the cuff pressure is maintained at the first pressure and the subject is in an upright position; assess an autonomic nerve function of the subject based on a result of the determination; and output a result of the assessment.

Preferably, the processor is further configured to: control the cuff pressure to be lowered from the first pressure when the amplitude of the pulse wave signal of the subject is smaller than the threshold value; calculate second blood pressure information of the subject during a process of lowering the cuff pressure from the first pressure; assess the autonomic nerve function of the subject further based on the first blood pressure information and the second blood pressure information.

Preferably, the processor is further configured to assess the autonomic nerve function of the subject based on a difference between a pulse rate included in the first blood pressure information and a pulse rate included in the second blood pressure information.

Preferably, the processor is further configured to assess the autonomic nerve function of the subject based on a difference between a pulse pressure included in the first blood pressure information and a pulse pressure included in the second blood pressure information.

Preferably, the processor is further configured to: control the cuff pressure to increase after the second blood pressure information is calculated; calculate the cuff pressure at which the amplitude of the pulse wave signal of the subject is smaller than the threshold value during a process of increasing the cuff pressure; calculate time elapsed between a first time when the amplitude of the pulse wave signal of the subject is determined to be smaller than the threshold value and a second time when the calculated cuff pressure is stabilized; and assess the autonomic nerve function of the subject further based on the elapsed time.

Preferably, the result of assessment relates to orthostatic dysregulation.

Preferably, the processor is further configured to indicate to the subject to make a transition from the recumbent position to the upright position after finishing calculation of the first blood pressure information.

According to another embodiment, an assessment system for assessing an autonomic nerve function of a subject is provided. The assessment system includes a blood pressure monitor and a terminal device configured to communicate with the blood pressure monitor. The blood pressure monitor includes a processor configured to: control a cuff pressure representing an internal pressure of a cuff attached to a measurement site of the subject; and calculate blood pressure information of the subject based on a cuff pressure signal representing the cuff pressure and a pulse wave signal superimposed on the cuff pressure signal. The calculation includes calculating first blood pressure information of the subject who has maintained a recumbent position for a prescribed time period. The processor of the blood pressure monitor is configured to: maintain the cuff pressure at a first pressure lower by a prescribed value than a systolic blood pressure included in the first blood pressure information; and determine whether or not an amplitude of the pulse wave signal of the subject is equal to or greater than a threshold value when the cuff pressure is maintained at the first pressure and the subject is in an upright position. The terminal device comprising a processor configured to: assess an autonomic nerve function of the subject based on a result of the determination by the processor of the blood pressure monitor; and output a result of the assessment.

A method of controlling a blood pressure monitor according to another embodiment includes controlling a cuff pressure representing an internal pressure of a cuff attached to a measurement site of a subject and calculating blood pressure information of the subject based on a cuff pressure signal representing the cuff pressure and a pulse wave signal superimposed on the cuff pressure signal. The calculation includes calculating first blood pressure information of the subject who has maintained a recumbent position for a prescribed time period. The controlling includes maintaining the cuff pressure at a first pressure lower by a prescribed value than a systolic blood pressure included in the first blood pressure information. The method further includes determining whether or not an amplitude of the pulse wave signal of the subject is equal to or greater than a threshold value when the cuff pressure is maintained at the first pressure and the subject is in an upright position, assessing an autonomic nerve function of the subject based on a result of the determination, and outputting a result of the assessment.

The foregoing and other objects, features, aspects and advantages of the present invention will become more apparent from the following detailed description of the exemplary embodiments when taken in conjunction with the accompanying drawings.

DESCRIPTION OF THE EMBODIMENTS

Figure 1:
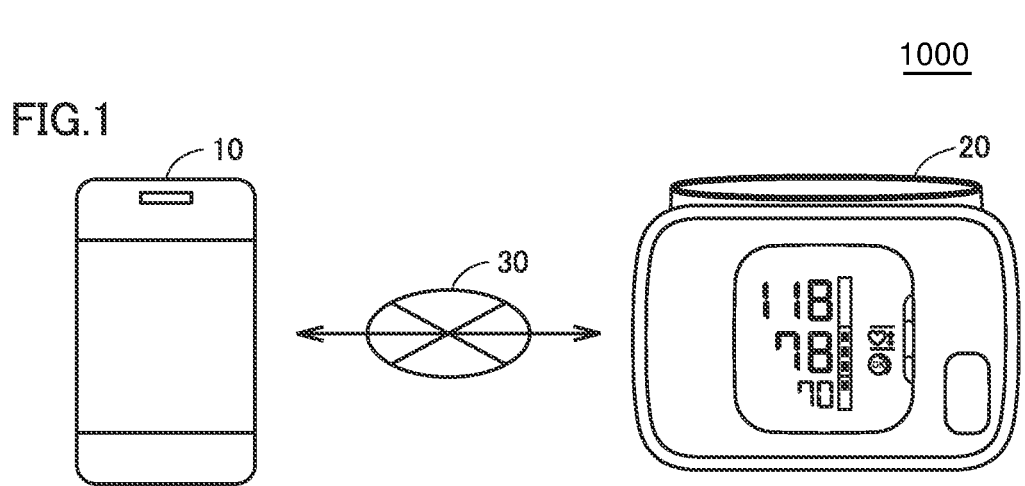
FIG. 1 is a diagram showing a schematic configuration of an assessment system.

An embodiment of the present disclosure will be described below with reference to the drawings. In the description below, the same elements have the same reference characters allotted and their labels and functions are also identical. Therefore, detailed description thereof will not be repeated.

<System Configuration>

FIG. 1 is a diagram showing a schematic configuration of an assessment system 1000.

Referring to FIG. 1, assessment system 1000 includes a terminal device 10 representing a user terminal, a blood pressure monitor 20 for measuring a blood pressure of a subject representing the user, and a network 30.

Blood pressure monitor 20 is a wrist blood pressure monitor in which a main body and a cuff are integrated. Blood pressure monitor 20 includes an apparatus main body and a cuff as its main components. In measurement of a blood pressure, blood pressure monitor 20 is attached with the cuff being wound around the wrist of a subject. Blood pressure monitor 20 may be an upper arm blood pressure monitor in which a main body and a cuff (an arm band) are integrated.

Terminal device 10 is implemented, for example, by a smartphone. Description will be given below with reference to a smartphone as a representative example of the "terminal device." The terminal device may be implemented by another terminal device such as a foldable portable telephone, a tablet terminal device, a personal computer (PC), or a personal data assistance (PDA).

Network 30 for connecting terminal device 10 and blood pressure monitor 20 to each other adopts a short-range wireless communication scheme and typically adopts Bluetooth® low energy (BLE). Therefore, terminal device 10 and blood pressure monitor 20 are BLE devices with a function to establish wireless communication based on BLE. Network 30, however, is not limited thereto, and other wireless communication schemes such as Bluetooth® or wireless local area network (LAN) or a wired communication scheme based on a universal serial bus (USB) may be adopted.

<Hardware Configuration>

(Terminal Device)

Figure 2:
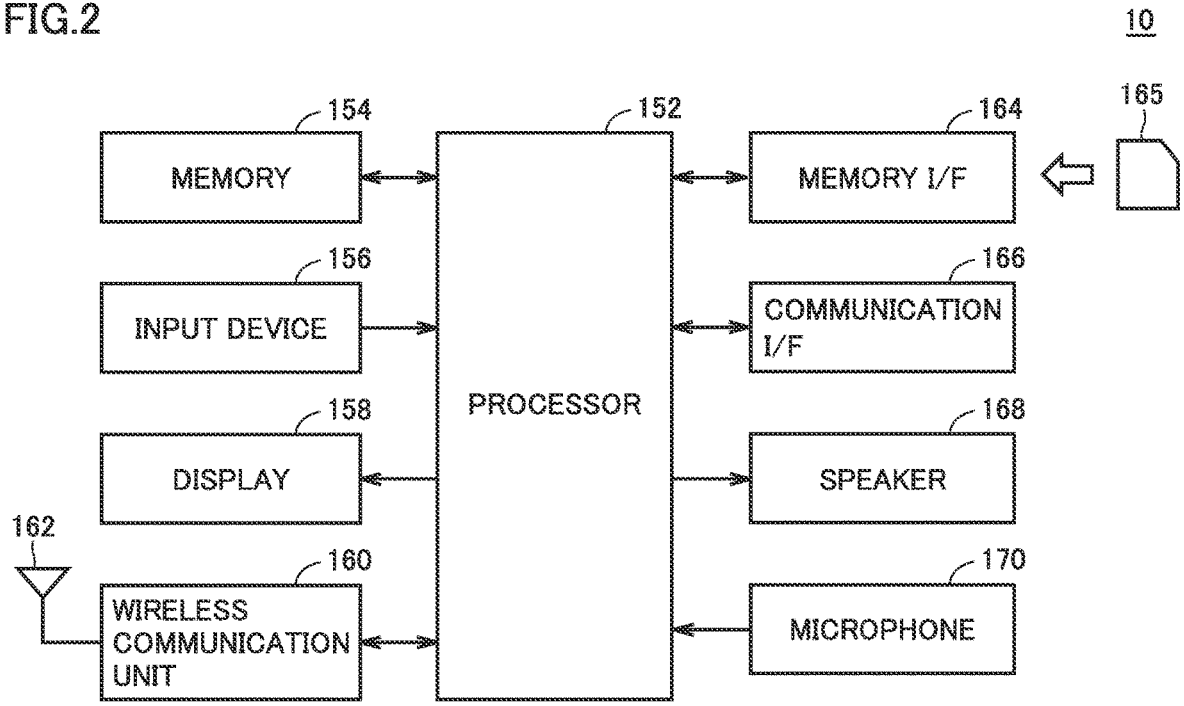
FIG. 2 is a block diagram representing an exemplary hardware configuration of a terminal device.

FIG. 2 is a block diagram representing an exemplary hardware configuration of terminal device 10. Referring to FIG. 2, terminal device 10 includes as its main components, a processor 152, a memory 154, an input device 156, a display 158, a wireless communication unit 160, a communication antenna 162, a memory interface (I/F) 164, a communication interface (I/F) 166, a speaker 168, and a microphone 170.

Processor 152 is typically implemented by an operation processor such as one or more central processing units (CPU) or one or more multi processing units (MPU). The hardware may be an FPGA (Field Programmable Gate Array), an ASIC (Application Specific Integrated Circuit), and another circuit having an operation function, other than a CPU. Processor 152 controls operations by each unit in terminal device 10 by reading and executing a program stored in memory 154.

Memory 154 is implemented by a random access memory (RAM), a read-only memory (ROM), or a flash memory. Memory 154 stores a program to be executed by processor 152 or data to be used by processor 152.

Input device 156 accepts an operation input to terminal device 10. Typically, input device 156 is implemented by a touch panel. The touch panel is provided on display 158 which performs a function as a display portion, and it is, for example, of a capacitance type. The touch panel senses a touch operation thereon by an external object every prescribed time and inputs a touch coordinate to processor 152. Input device 156 may include a button or the like.

Wireless communication unit 160 is connected to a mobile communication network through communication antenna 162 and transmits and receives a wireless communication signal. Terminal device 10 can thus communicate with another communication device through a mobile communication network such as long term evolution (LTE).

Memory interface 164 reads data from an external storage medium 165. Processor 152 reads data stored in storage medium 165 through memory interface 164 and has the data stored in memory 154. Processor 152 reads data from memory 154 and has the data stored in external storage medium 165 through memory interface 164.

Storage medium 165 includes media which store a program in a non-volatile manner, such as a compact disc (CD), a digital versatile disk (DVD), a Blu-ray Disc™ (BD), a universal serial bus (USB) memory, and a secure digital (SD) memory card.

Communication interface (I/F) 166 serves to exchange various types of data with another device, and is implemented by an adapter or a connector. In the present embodiment, BLE is adopted as a communication scheme.

Speaker 168 converts an audio signal provided from processor 152 into voice and sound and outputs the voice and sound to the outside of terminal device 10. Microphone 170 accepts audio input to terminal device 10 and provides an audio signal corresponding to the audio input to processor 152. Terminal device 10 further includes an acceleration sensor and an angular speed sensor or a time counter for counting time or the like.

(Blood Pressure Monitor)

Figure 3:
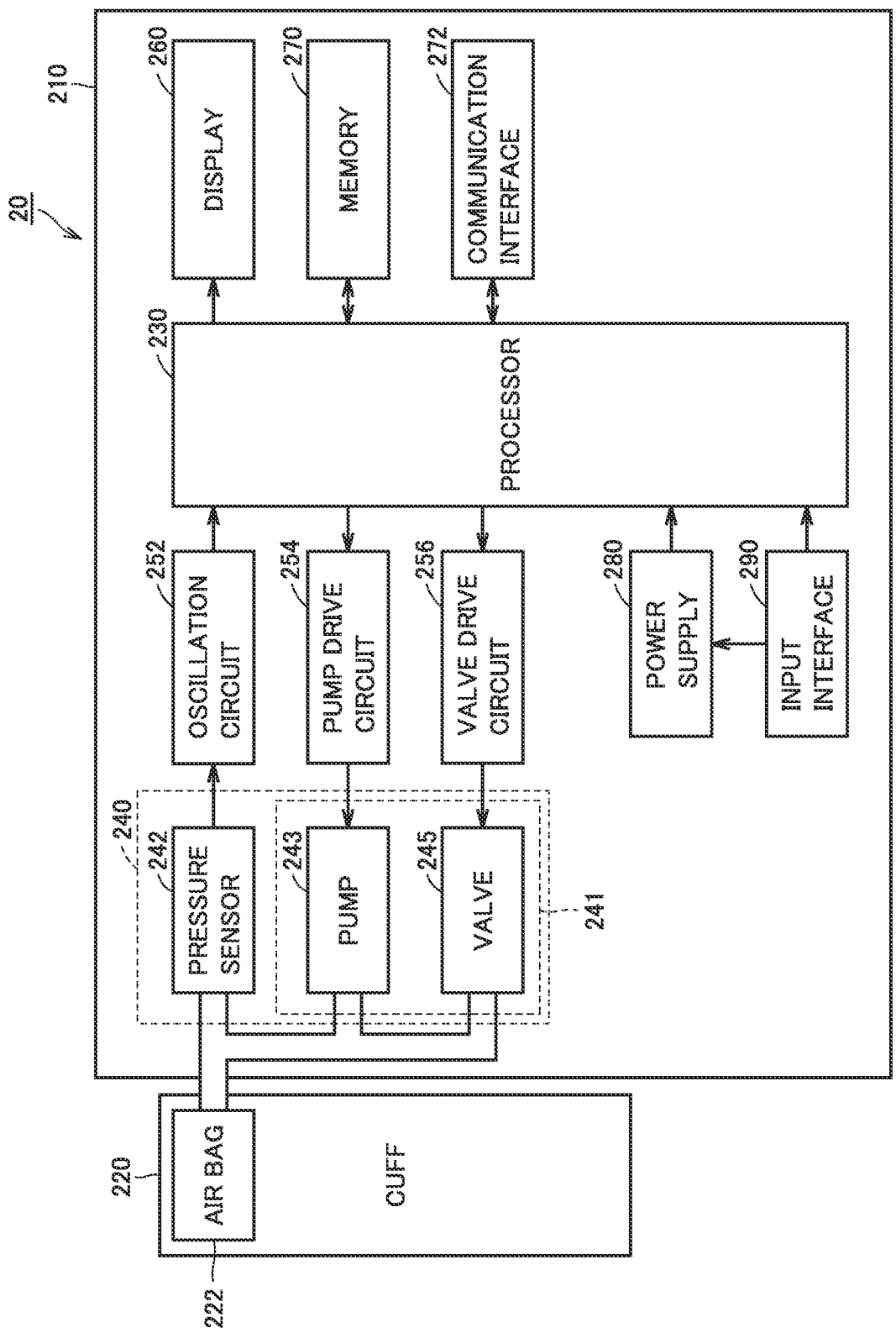
FIG. 3 is a block diagram representing an exemplary hardware configuration of a blood pressure monitor.

FIG. 3 is a block diagram representing an exemplary hardware configuration of blood pressure monitor 20. Referring to FIG. 3, blood pressure monitor 20 includes an apparatus main body 210 and a cuff 220 as its main components. Cuff 220 contains an air bag 222. Apparatus main body 210 includes a processor 230, an air-associated component 240 for blood pressure measurement, an oscillation circuit 252, a pump drive circuit 254, a valve drive circuit 256, a display 260, a memory 270, a communication interface 272, a power supply 280, and an input interface 290.

Processor 230 is implemented by an operation processor such as a CPU or an MPU. Processor 230 performs each type of processing (step) by blood pressure monitor 20 which will be described later by reading and executing a program stored in memory 270.

Air-associated component 240 supplies or bleeds air through a tube to air bag 222 contained in cuff 220. Air-associated component 240 includes a pressure sensor 242 for detecting a pressure in air bag 222 and a pump 243 and a valve 245 as an inflation and deflation mechanism 241 for inflating and deflating air bag 222.

Pressure sensor 242 detects a pressure in air bag 220 (cuff pressure) and outputs a signal in accordance with the detected pressure (cuff pressure signal) to oscillation circuit 252. Pressure sensor 242 is implemented, for example, by a piezoresistive pressure sensor, and connected to pump 243, valve 245, and air bag 222 contained in cuff 220 through a cuff air tube. Pump 243 supplies air to air bag 222 through a tube for increasing a cuff pressure. Valve 245 is opened or closed for controlling a cuff pressure by maintaining a pressure in air bag 222 or bleeding air in air bag 222.

Oscillation circuit 252 outputs to processor 230, a signal at an oscillation frequency in accordance with a value output from pressure sensor 242. For example, oscillation circuit 252 oscillates based on a value of an electric signal from pressure sensor 242 in accordance with variation in electric resistance caused by a piezoresistive effect. Oscillation circuit 252 outputs to processor 230, a frequency signal having a frequency in accordance with the value of the electric signal from pressure sensor 242. Pump drive circuit 254 controls drive of pump 243 based on a control signal issued by processor 230. Valve drive circuit 256 controls opening and closing of valve 245 based on a control signal issued by processor 230.

In measurement of a blood pressure in accordance with a general oscillometric method, operations as below are generally performed. Specifically, a cuff is wound around a measurement site (a wrist or an arm) of a subject in advance, and during measurement, the pump and the valve are controlled to increase a cuff pressure to a pressure higher than a systolic blood pressure and thereafter to gradually lower the cuff pressure. In this process of pressure lowering, the pressure sensor detects the cuff pressure and extract as a pulse wave signal, variation in arterial volume that occurs in an artery at the measurement site. A systolic blood pressure and a diastolic blood pressure are calculated based on variation in amplitude (mainly rise and fall) of the pulse wave signal with variation in cuff pressure at that time.

Display 260 shows various types of information including a result of measurement of a blood pressure based on a control signal from processor 230. Memory 270 stores a program for having processor 230 perform a prescribed operation or various types of information such as a value of a measured blood pressure. Communication interface 272 exchanges various types of information with terminal device 10. Power supply 280 supplies electric power to processor 230 and each piece of hardware. Input interface 290 accepts various instructions from a subject. Blood pressure monitor 20 further includes a time counter for counting time or the like.

<Overview of Operations>

Figure 4:
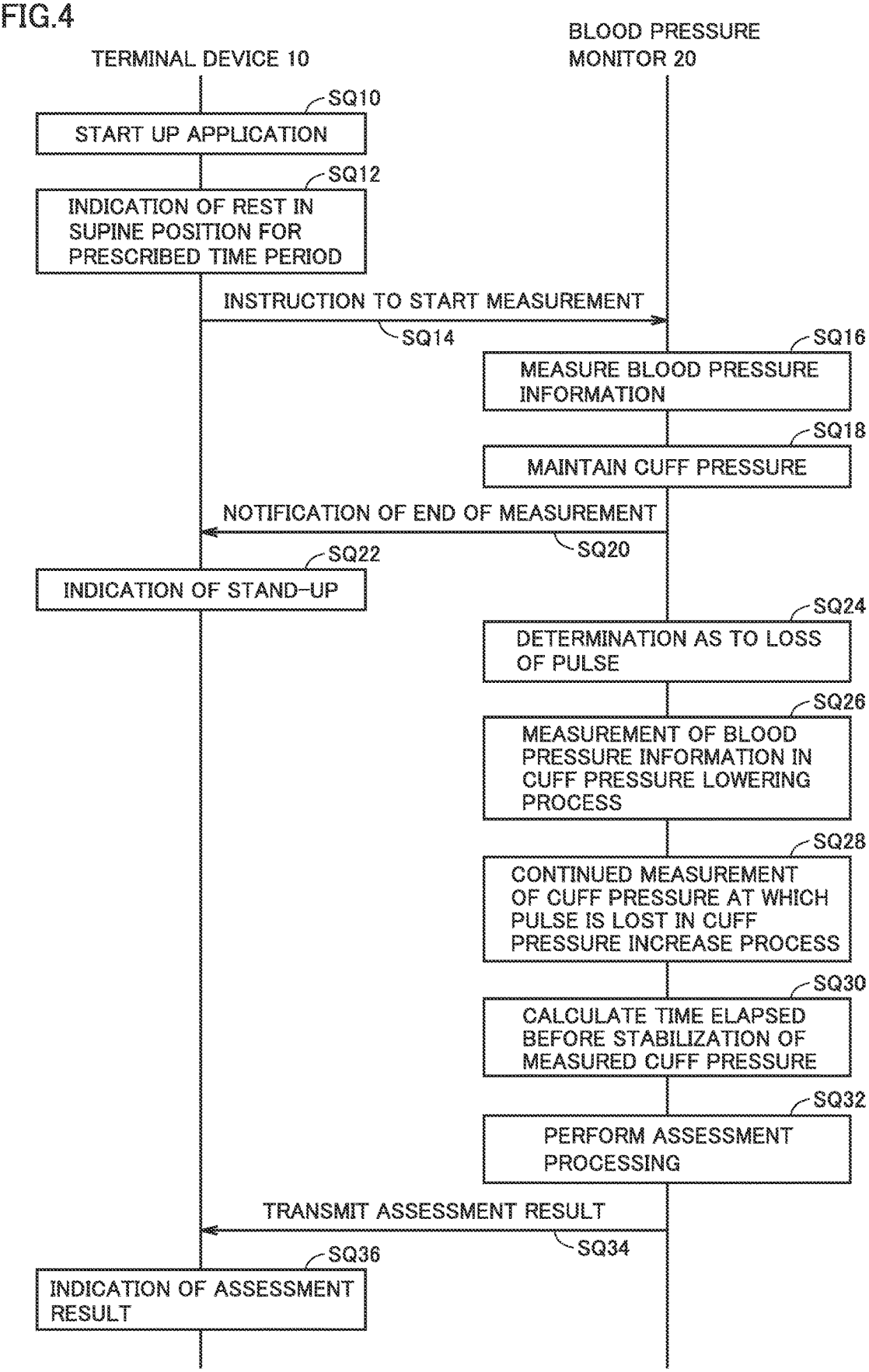
FIG. 4 is a diagram showing overview of operations by the assessment system.

FIG. 4 is a diagram showing overview of operations by assessment system 1000. Blood pressure monitor 20 assesses an autonomic nerve function of a subject representing a user of terminal device 10. Specifically, blood pressure monitor 20 makes an assessment as to orthostatic dysregulation of the subject.

Referring to FIG. 4, terminal device 10 starts up an application for assessing the autonomic nerve function in response to an instruction from a subject (sequence SQ10). Terminal device 10 gives the subject information inviting the subject to rest for a prescribed time period (for example, ten minutes) in a supine position after start-up of the assessment application (sequence SQ12). In response to the given information, the subject rests in the supine position for the prescribed time period. Terminal device 10 instructs blood pressure monitor 20 to start measurement of a blood pressure after lapse of a prescribed time period (sequence SQ14).

After lapse of the prescribed time period, blood pressure monitor 20 measures blood pressure information X1 of the subject (sequence SQ16). Specifically, blood pressure monitor 20 measures a systolic blood pressure SY1, a diastolic blood pressure D1, a pulse rate PR1, and a pulse pressure PU1 (=SY1−D1) as blood pressure information X1. Then, blood pressure monitor 20 maintains a cuff pressure at a pressure Pk lower by a prescribed value than measured systolic blood pressure SY1 (sequence SQ18). A person who suffers from orthostatic dysregulation is highly likely to exhibit significant lowering in systolic blood pressure (for example, lowering by 21 mmHg or more) when he/she stands up from the supine position to an upright position. Therefore, the prescribed value is set, for example, to 21 mmHg.

Blood pressure monitor 20 transmits to terminal device 10, a notification to the effect that measurement of blood pressure information has ended (sequence SQ20). When terminal device 10 receives the notification, it gives the subject information inviting the subject to perform a stand-up action (sequence SQ22). The subject performs the stand-up action in accordance with the given information. Blood pressure monitor 20 determines whether or not a pulse has been lost based on an amplitude of the pulse wave signal (sequence SQ24).

In sequence SQ18, the cuff pressure is maintained at pressure Pk lower by the prescribed value than the systolic blood pressure. Therefore, no loss of a pulse means that the systolic blood pressure is not significantly lowered even though transition to the upright position is made. Loss of a pulse means significant lowering in systolic blood pressure when transition to the upright position is made. This fact can be one factor for assessment as suspected orthostatic dysregulation. Blood pressure monitor 20 is assumed to have determined that a pulse has been lost.

When blood pressure monitor 20 determines that a pulse has been lost, it gradually lowers the cuff pressure and measures blood pressure information X2 in this process of pressure lowering (a pressure lowering process) (sequence SQ26). Specifically, when blood pressure monitor 20 detects resumption of a pulse based on a pulse wave signal, it measures a systolic blood pressure SY2 based on a cuff pressure at the time of detection and measures a pulse rate PR2. Blood pressure monitor 20 further lowers the cuff pressure, and when the blood pressure monitor detects loss of a pulse based on a pulse wave signal, it measures a diastolic blood pressure D2 based on the cuff pressure at the time of detection. Blood pressure information X2 includes systolic blood pressure SY2, diastolic blood pressure D2, pulse rate PR2, and a pulse pressure PU2 (=SY2−D2).

Then, blood pressure monitor 20 increases the cuff pressure, and in this process of pressure increase (a pressure increase process), the blood pressure monitor continues measurement of the cuff pressure at which loss of a pulse is detected (sequence SQ28). When one stands up from the supine position, a blood pressure temporarily lowers immediately after stand-up and the blood pressure thereafter increases. Therefore, it takes certain time until the blood pressure is stabilized. Therefore, in a process of increase in blood pressure, an amplitude of the pulse wave signal is not stable and a cuff pressure at which loss of a pulse is detected is not stable (that is, the systolic blood pressure is not stable). Therefore, blood pressure monitor 20 can know a time point when the blood pressure of the subject is stabilized by continuing measurement of the cuff pressure at which loss of a pulse is detected.

Blood pressure monitor 20 calculates time Te elapsed before the cuff pressure at which loss of a pulse is detected is stabilized in the pressure increase process (sequence SQ30). Specifically, blood pressure monitor 20 calculates time Te elapsed before stabilization of the cuff pressure since determination as a pulse having been lost in sequence SQ24. Blood pressure monitor 20 performs processing for assessment as to orthostatic dysregulation based on a result of determination in sequence SQ24 and a result of measurement including blood pressure information X1 and X2 and elapsed time Te (sequence SQ32). For example, blood pressure monitor 20 uses as criteria, a result of determination in sequence SQ24, a difference in pulse pressure between before and after stand-up, an amount of increase in pulse rate between before and after stand-up, and elapsed time Te. Details of assessment processing will be described later.

Blood pressure monitor 20 transmits a result of assessment as to orthostatic dysregulation to terminal device 10 (sequence SQ34). Terminal device 10 gives the subject an indication of the received result of assessment (sequence SQ36). The result of assessment is expressed, for example, in five levels of levels 1 to 5 in the ascending order of possibility of orthostatic dysregulation.

<Functional Configuration>

Figure 5:
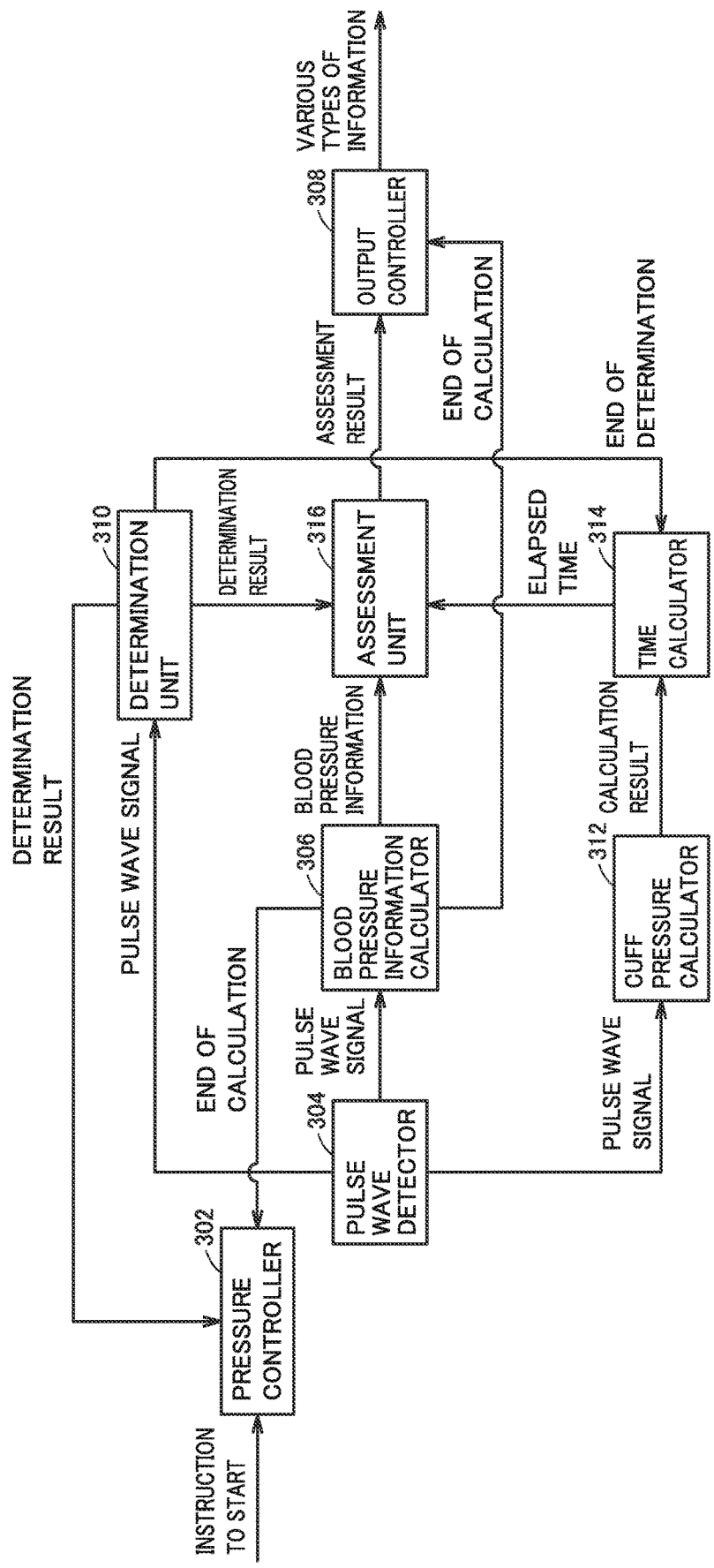
FIG. 5 is a block diagram showing a functional configuration of the blood pressure monitor.

FIG. 5 is a block diagram showing a functional configuration of blood pressure monitor 20. Referring to FIG. 5, blood pressure monitor 20 includes as its main functional configuration, a pressure controller 302, a pulse wave detector 304, a blood pressure information calculator 306, an output controller 308, a determination unit 310, a cuff pressure calculator 312, a time calculator 314, and an assessment unit 316. Each function is implemented, for example, by execution by processor 152 of blood pressure monitor 20, of a program stored in memory 154. Some or the entirety of the functions may be implemented by hardware.

Pressure controller 302 controls a cuff pressure in accordance with an instruction from a subject through input interface 290 or an instruction from terminal device 10. Specifically, pressure controller 302 controls pump 243 and valve 245 such that pump 243 is driven with pump drive circuit 254 being interposed and valve 245 is driven with valve drive circuit 256 being interposed. Valve 245 is opened or closed for controlling the cuff pressure by bleeding or sealing air in air bag 222.

Pulse wave detector 304 receives a signal indicating a cuff pressure detected by pressure sensor 242 and extracts a pulse wave signal representing a pulse wave at a measurement site and superimposed on the cuff pressure signal. Pulse wave detector 304 detects from the cuff pressure signal, a pulse wave representing a pressure component superimposed on the cuff pressure signal in synchronization with pulsation of the heart of the subject.

Blood pressure information calculator 306 calculates blood pressure information of the subject based on the cuff pressure signal and the pulse wave signal superimposed on the cuff pressure signal. Specifically, when blood pressure information calculator 306 adopts a reduced-pressure measurement scheme in which a pulse wave is detected during pressure reduction in air bag 222, blood pressure information calculator 306 calculates a systolic blood pressure based on the cuff pressure at the time of abrupt increase (rise) in amplitude of the pulse wave signal, a diastolic blood pressure based on the cuff pressure at the time of abrupt decrease (fall) in the same, a pulse rate, and a pulse pressure. Blood pressure information calculator 306 may adopt what is called an increased-pressure measurement scheme in which a pulse wave is detected during pressure increase in air bag 222.

In one aspect, blood pressure information calculator 306 calculates blood pressure information X1 of the subject who has maintained the supine position for a prescribed time period (for example, ten minutes). Pressure controller 302 maintains the cuff pressure at pressure Pk lower by a prescribed value than systolic blood pressure SY1 included in blood pressure information X1 after end of calculation of blood pressure information X1.

After end of calculation of blood pressure information X1, output controller 308 notifies terminal device 10 of end of calculation through communication interface 272. Terminal device 10 indicates the subject to perform a stand-up action through display 158 or speaker 168.

When the cuff pressure is maintained at pressure Pk and the subject is in the upright position, determination unit 310 determines whether or not an amplitude of the pulse wave signal of the subject is equal to or greater than a threshold value Th1 (that is, whether or not a pulse has been lost). When the amplitude of the pulse wave signal is equal to or greater than threshold value Th1, determination unit 310 determines that a pulse has not been lost, and when the amplitude of the pulse wave signal is smaller than threshold value Th1, it determines that a pulse has been lost.

When determination unit 310 determines that the amplitude of the pulse wave signal of the subject is smaller than threshold value Th1, pressure controller 302 controls the cuff pressure to gradually be lowered from pressure Pk. Blood pressure information calculator 306 calculates blood pressure information X2 of the subject in a process of lowering in cuff pressure from pressure Pk (pressure lowering process). Specifically, blood pressure information calculator 306 calculates systolic blood pressure SY2 corresponding to the cuff pressure at the time of rise of the amplitude of the pulse wave signal (at the time of resumption of a pulse), diastolic blood pressure D2 corresponding to the cuff pressure at the time of fall thereof (at the time of loss of a pulse), pulse rate PR2, and pulse pressure PU2.

After blood pressure information X2 is calculated, pressure controller 302 controls the cuff pressure to increase. Cuff pressure calculator 312 continues calculation of the cuff pressure at which the amplitude of the pulse wave signal of the subject is smaller than threshold value Th1 in the process of increase in cuff pressure. Specifically, cuff pressure calculator 312 successively calculates with a constant cycle, a systolic blood pressure corresponding to a cuff pressure at which the amplitude of the pulse wave signal is smaller than threshold value Th1.

Time calculator 314 calculates time Te elapsed between time t1 when determination unit 310 determines that the amplitude of the pulse wave signal of the subject is smaller than threshold value Th1 and time t2 at which the cuff pressure (that is, the systolic blood pressure) calculated by cuff pressure calculator 312 is stabilized. The state that the cuff pressure is stabilized refers, for example, to a state that a difference between a maximum value and a minimum value of the cuff pressure successively calculated by cuff pressure calculator 312 during a prescribed period is equal to or smaller than a prescribed pressure value (for example, 1 mmHg).

Assessment unit 316 assesses the autonomic nerve function of the subject (specifically, makes an assessment as to orthostatic dysregulation) based on predetermined criterion information. Criterion information includes a criterion L1 relating to a result of determination by determination unit 310, a criterion L2 relating to a difference between pulse rate PR1 included in blood pressure information X1 and pulse rate PR2 included in blood pressure information X2, a criterion L3 relating to a difference between pulse pressure PU1 included in blood pressure information X1 and pulse pressure PU2 included in blood pressure information X2, and a criterion L4 relating to elapsed time Te. In the present embodiment, each criterion is defined such that, when the criterion is satisfied, orthostatic dysregulation (reduced autonomic nerve function) is not suspected, and when the criterion is not satisfied, orthostatic dysregulation (reduced autonomic nerve function) is suspected.

Assessment unit 316 assesses the autonomic nerve function of the subject at least based on criterion L1 relating to a result of determination by determination unit 310. Specifically, when determination unit 310 determines that the amplitude of the pulse wave signal of the subject is equal to or greater than threshold value Th1 (that is, a pulse has not been lost), assessment unit 316 makes an assessment that criterion L1 is satisfied (that is, orthostatic dysregulation is not suspected). When determination unit 310 determines that the amplitude of the pulse wave signal of the subject is smaller than threshold value Th1 (that is, a pulse has been lost), assessment unit 316 makes an assessment that criterion L1 is not satisfied (that is, orthostatic dysregulation is suspected).

Assessment unit 316 assesses the autonomic nerve function of the subject in accordance with criterion L2 relating to a difference between pulse rate PR1 and pulse rate PR2. Specifically, when an amount of increase in pulse rate (PR2−PR1) representing a difference between pulse rate PR1 and pulse rate PR2 is smaller than a threshold value Th2 (for example, 21 pulses/minute), assessment unit 316 makes an assessment that criterion L2 is satisfied. When an amount of increase in pulse rate is equal to or greater than threshold value Th2, assessment unit 316 makes an assessment that criterion L2 is not satisfied.

Assessment unit 316 assesses the autonomic nerve function of the subject in accordance with criterion L3 relating to a difference between pulse pressure PU1 and pulse pressure PU2. Specifically, when an amount of lowering in pulse pressure (PU1−PU2) representing a difference between pulse pressure PU1 and pulse pressure PU2 is smaller than a threshold value Th3 (for example, 16 mmHg), assessment unit 316 makes an assessment that criterion L3 is not satisfied. When an amount of lowering in pulse pressure is equal to or greater than threshold value Th3, assessment unit 316 makes an assessment that criterion L3 is not satisfied.

Assessment unit 316 assesses the autonomic nerve function of the subject in accordance with criterion L4 relating to elapsed time Te. Specifically, when elapsed time Te is smaller than a threshold value Th4 (for example, seventeen seconds), assessment unit 316 makes an assessment that criterion L4 is satisfied. When elapsed time Te is equal to or greater than threshold value Th4, assessment unit 316 makes an assessment that criterion L4 is not satisfied.

For example, when all of criteria L1 to L4 are satisfied, assessment unit 316 makes an assessment as level 1 which indicates extremely low possibility of orthostatic dysregulation. When three of criteria L1 to L4 are satisfied, the assessment unit makes an assessment as level 2 which indicates low possibility of orthostatic dysregulation. When two of criteria L1 to L4 are satisfied, the assessment unit makes an assessment as level 3 which indicates relatively low possibility of orthostatic dysregulation. When one of criteria L1 to L4 is satisfied, the assessment unit makes an assessment as level 4 which indicates relatively high possibility of orthostatic dysregulation. When none of criteria L1 to L4 are satisfied, assessment unit 316 makes an assessment as level 5 which indicates high possibility of orthostatic dysregulation.

Output controller 308 transmits a result of assessment by assessment unit 316 to terminal device 10 through communication interface 272.

<Processing Procedure>

Figure 6:
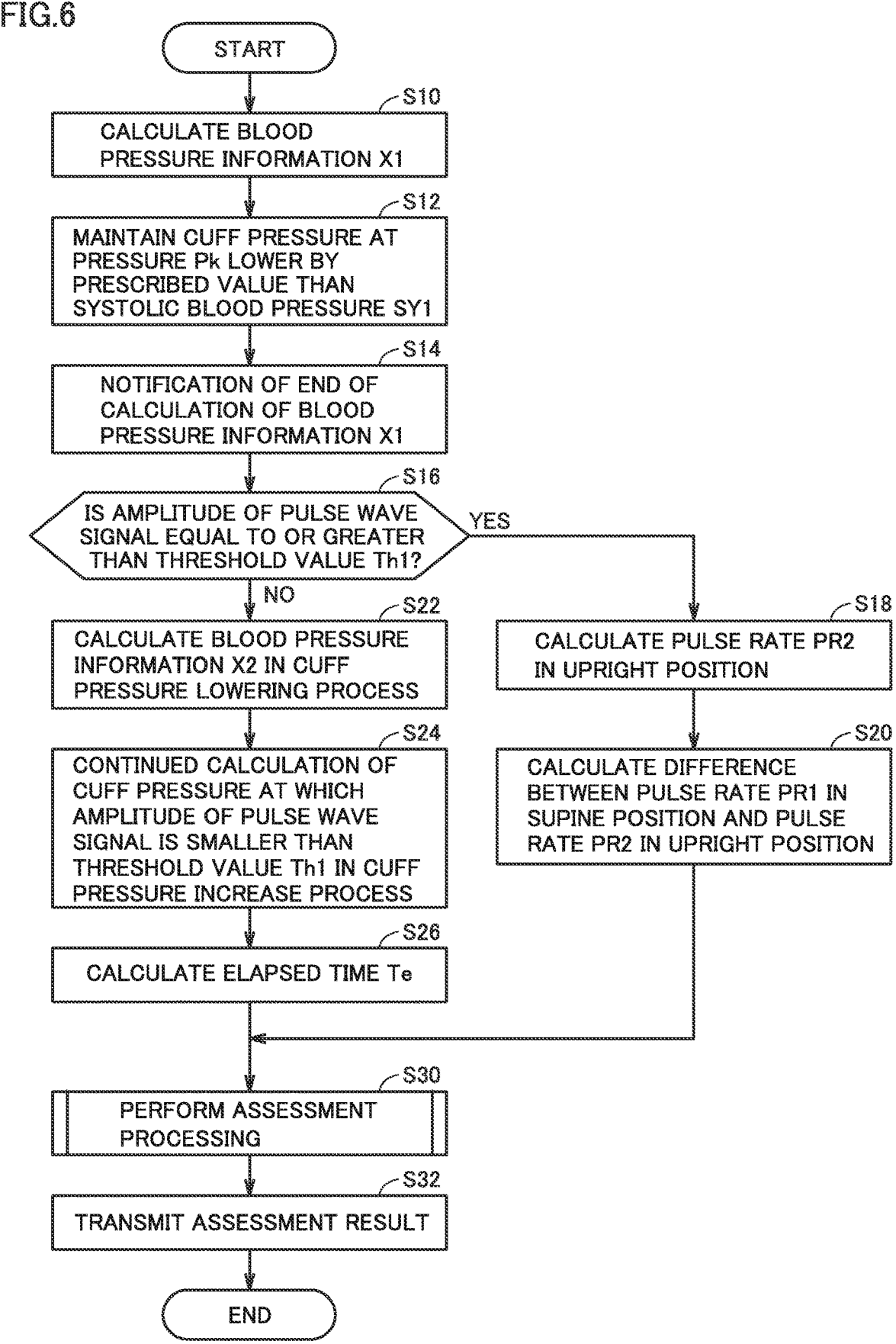
FIG. 6 is a flowchart showing an exemplary procedure of processing by the blood pressure monitor.

FIG. 6 is a flowchart showing an exemplary procedure of processing by blood pressure monitor 20. At the time point of start of processing, a subject who wears cuff 220 of blood pressure monitor 20 has been resting for a prescribed time period in the supine position.

Referring to FIG. 6, processor 230 of blood pressure monitor 20 calculates blood pressure information X1 of the subject who has maintained the supine position for the prescribed time period (step S10). Blood pressure monitor 20 maintains a cuff pressure at pressure Pk lower by a prescribed value than systolic blood pressure SY1 included in blood pressure information X1 (step S12). Processor 230 notifies terminal device 10 of end of calculation of blood pressure information X1 through communication interface 272 (step S14). Terminal device 10 thus indicates the subject to perform a stand-up action.

Processor 230 determines whether or not an amplitude of a pulse wave signal of the subject in the upright position is equal to or greater than threshold value Th1 (step S16). When the amplitude is equal to or greater than threshold value Th1 (that is, a pulse has not been lost) (YES in step S16), processor 230 calculates pulse rate PR2 in the upright position (step S18). Then, processor 230 calculates a difference between pulse rate PR1 in the supine position and pulse rate PR2 in the upright position (step S20) and performs processing in step S30 which will be described later.

When the amplitude of the pulse wave signal of the subject in the upright position is smaller than threshold value Th1 (that is, a pulse has been lost) (NO in step S16), processor 230 calculates blood pressure information X2 of the subject in the cuff pressure lowering process (step S22). Then, processor 230 continues calculation of the cuff pressure at which the amplitude of the pulse wave signal is smaller than threshold value Th1 in the cuff pressure increase process (step S24). Processor 230 calculates time Te elapsed between time t1 when it is determined that a pulse has been lost in step S16 and time t2 when the cuff pressure continually calculated in step S24 is stabilized (step S26), and performs assessment processing (step S30).

Figure 7:
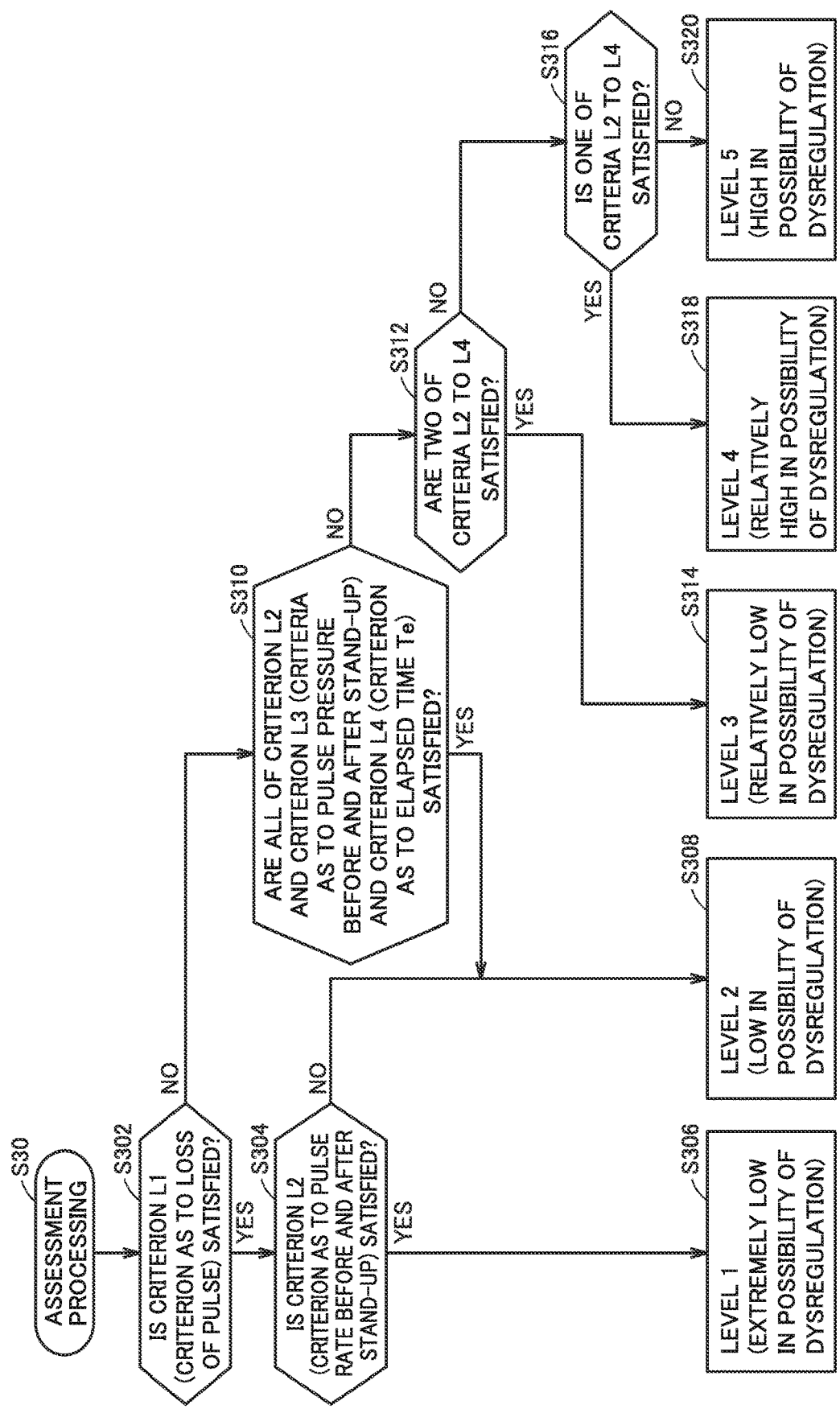
FIG. 7 is a flowchart showing an exemplary procedure of assessment processing by the blood pressure monitor.

FIG. 7 is a flowchart showing an exemplary procedure of assessment processing by blood pressure monitor 20. Referring to FIG. 7, processor 230 determines whether or not criterion L1 relating to a result of determination as to loss of a pulse is satisfied (step S302). When the amplitude of the pulse wave signal is equal to or greater than threshold value Th1, processor 230 determines that criterion L1 is satisfied, and when the amplitude is smaller than threshold value Th1, processor 230 determines that criterion L1 is not satisfied.

When criterion L1 is satisfied (YES in step S302), processor 230 determines whether or not criterion L2 relating to a pulse rate before and after stand-up is satisfied (step S304). When an amount of increase in pulse rate (PR2−PR1) is smaller than threshold value Th2, processor 230 determines that criterion L2 is satisfied, and when an amount of increase in pulse rate is equal to or greater than threshold value Th2, the processor determines that criterion L2 is not satisfied.

When criterion L2 is satisfied (YES in step S304), an assessment that the subject is extremely low in possibility of orthostatic dysregulation (level 1) is made (step S306). When criterion L2 is not satisfied (NO in step S304), an assessment that the subject is low in possibility of orthostatic dysregulation (level 2) is made (step S308).

When criterion L1 is not satisfied in step S302 (NO in step S302), processor 230 determines whether or not all of criterion L2, criterion L3 relating to a pulse pressure before and after stand-up, and criterion L4 relating to elapsed time Te are satisfied (step S310).

When an amount of lowering in pulse pressure (PU1−PU2) is smaller than threshold value Th3, processor 230 determines that criterion L3 is satisfied, and when an amount of lowering in pulse pressure is equal to or greater than threshold value Th3, the processor determines that criterion L3 is not satisfied. When elapsed time Te is smaller than threshold value Th4, processor 230 determines that criterion L4 is satisfied, and when elapsed time Te is equal to or greater than threshold value Th4, the processor determines that criterion L4 is not satisfied.

When all of criteria L2 to L4 are satisfied (YES in step S310), processor 230 makes an assessment that the subject is low in possibility of orthostatic dysregulation (level 2) (step S308). Otherwise (NO in step S310), processor 230 determines whether or not two of criteria L2 to L4 are satisfied (step S312).

When two of criteria L2 to L4 are satisfied (YES in step S312), processor 230 makes an assessment that the subject is relatively low in possibility of orthostatic dysregulation (level 3) (step S314). Otherwise (NO in step S312), processor 230 determines whether or not one of criteria L2 to L4 is satisfied (step S316).

When one of criteria L2 to L4 is satisfied (YES in step S316), processor 230 makes an assessment that the subject is relatively high in possibility of orthostatic dysregulation (level 4) (step S318). Otherwise (that is, when none of criteria L2 to L4 are satisfied) (NO in step S316), processor 230 makes an assessment that the subject is high in possibility of orthostatic dysregulation (level 5) (step S320).

Referring again to FIG. 6, blood pressure monitor 20 transmits a result of assessment obtained in assessment processing to terminal device 10 through communication interface 272 (step S32). Terminal device 10 thus receives the result of assessment and gives information based on the received result of assessment.

<Advantages>

According to the present embodiment, orthostatic dysregulation can be screened in a simplified manner. Since a subject himself/herself can conduct a test which has been conducted by a doctor and a nurse with an advanced method, the subject can know a health concern of the subject himself/herself.

Other Embodiments (1) Though a configuration in which a subject is in the supine position before stand-up has been described in the embodiment above, limitation to such a configuration is not intended. For example, a position before stand-up should only be a recumbent position including a prone position and a lateral recumbent position.

(2) The embodiment described above may be configured such that some of the functions of blood pressure monitor 20 may be performed by terminal device 10. For example, the function of assessment unit 316 of blood pressure monitor 20 may be performed by terminal device 10. In this case, blood pressure monitor 20 transmits a result of determination as to loss of a pulse and a result of measurement including blood pressure information X1 and X2 and elapsed time Te to terminal device 10. Terminal device 10 performs the assessment processing as in assessment unit 316 described above based on the result of measurement.

(3) The embodiment described above may be configured such that a series of processes from an instruction to start measurement until indication of a result of assessment is performed by blood pressure monitor 20 alone. For example, blood pressure monitor 20 accepts input of an instruction to start assessment from a subject through input interface 290. Then, blood pressure monitor 20 indicates the subject to make transition from the supine position to the upright position after it performs processing in steps S10 and S12 in FIG. 6. Specifically, processor 230 (indicator) of blood pressure monitor 20 has display 260 show information inviting the subject to make transition from the supine position to the upright position. When a speaker is mounted on blood pressure monitor 20, processor 230 may have the speaker provide audio output of the information.

Blood pressure monitor 20 outputs a result of assessment after it performs steps S16 to S30 in FIG. 6. For example, blood pressure monitor 20 (output controller 308) shows a result of assessment on display 260 or provides audio output thereof through the speaker.

(4) Though a configuration in which terminal device 10 instructs blood pressure monitor 20 to start measurement of a blood pressure after lapse of a prescribed time period is described with reference to FIG. 4 in the embodiment above, limitation to the configuration is not intended. For example, terminal device 10 may be configured to give the subject information inviting the subject to start measurement of a blood pressure through speaker 168 after lapse of the prescribed time period. In this case, blood pressure monitor 20 starts measurement of blood pressure information X1 of the subject by accepting an instruction to start measurement from the subject through input interface 290 (for example, a measurement start button).

(5) In the embodiment described above, a program for causing a computer to function to carry out control as described in the flowchart described above can also be provided. Such a program can also be recorded on a non-transitory computer-readable recording medium such as a flexible disk, a compact disk read only memory (CD-ROM), a secondary storage device, a main storage device, and a memory card adapted to the computer, and can be provided as a program product. Alternatively, the program can also be recorded and provided in a recording medium such as a hard disk contained in the computer. Further, the program can also be provided by downloading through a network.

The program may call a necessary module out of program modules provided as a part of an operating system (OS) of the computer in a prescribed sequence and at prescribed timing and perform processing. In such a case, the program itself does not include the module above but executes the processing in cooperation with the OS. Such a program not including the module may also be encompassed in the program according to the present embodiment.

The program according to the present embodiment may be provided in a manner incorporated as a part of another program. In such a case as well, the program itself does not include the module included in another program, but processing is performed in cooperation with another program. Such a program incorporated in another program may also be encompassed in the program according to the present embodiment.

(6) The configuration exemplified as the embodiment described above represents an exemplary configuration of the present invention. The configuration can also be combined with another known technique, or can also be modified, for example, by not providing some aspects, without departing from the gist of the present invention. In the embodiment described above, processing or features described in other embodiments may be adopted and carried out as appropriate.

According to the present disclosure, an autonomic nerve function of a subject can more accurately be assessed.

It should be understood that the embodiments disclosed herein are illustrative and non-restrictive in every respect. The scope of the present invention is defined by the terms of the claims rather than the description above and is intended to include any modifications within the scope and meaning equivalent to the terms of the claims.

The invention claimed is:

1. A blood pressure monitor comprising a processor configured to:
   control a cuff pressure, which is an internal pressure of a cuff attached to a measurement site of a subject;
   extract a pulse wave signal from the measurement site as the cuff pressure is varied;
   calculate blood pressure information of the subject based on a cuff pressure signal representing the cuff pressure and the extracted pulse wave signal superimposed on the cuff pressure signal, the calculation including calculating first blood pressure information of the subject who has maintained a recumbent position for a prescribed time period,
   maintain the cuff pressure at a first pressure lower by a prescribed value than a systolic blood pressure included in the first blood pressure information;
   determine whether an amplitude of the pulse wave signal of the subject is equal to or greater than a threshold value when the cuff pressure is maintained at the first pressure and the subject is in an upright position;
   assess an autonomic nerve function of the subject based on a result of the determination; and
   output a result of the assessment, wherein the result indicates suspected dysfunction of the autonomic nerve function if the amplitude of the pulse wave signal is less than the threshold value.

2. The blood pressure monitor according to claim 1, wherein the processor is further configured to:
   control the cuff pressure to be lowered from the first pressure when the amplitude of the pulse wave signal of the subject is smaller than the threshold value;
   calculate second blood pressure information of the subject during a process of lowering the cuff pressure from the first pressure; and
   assess the autonomic nerve function of the subject further based on the first blood pressure information and the second blood pressure information.

3. The blood pressure monitor according to claim 2, wherein the processor is further configured to assess the autonomic nerve function of the subject based on a difference between a pulse rate included in the first blood pressure information and a pulse rate included in the second blood pressure information.

4. The blood pressure monitor according to claim 2, wherein the processor is further configured to assess the autonomic nerve function of the subject based on a difference between a pulse pressure included in the first blood pressure information and a pulse pressure included in the second blood pressure information.

5. The blood pressure monitor according to claim 2, wherein the processor is further configured to:
   control the cuff pressure to increase after the second blood pressure information is calculated;
   determine the cuff pressure at which the amplitude of the pulse wave signal of the subject is smaller than the threshold value during a process of increasing the cuff pressure;
   calculate time elapsed between a first time when the amplitude of the pulse wave signal of the subject is determined to be smaller than the threshold value and a second time when a difference between a maximum value and a minimum value of a calculated systolic blood pressure corresponding to the cuff pressure during a prescribed period is equal to or smaller than a threshold pressure value; and assess the autonomic nerve function of the subject further based on the elapsed time.

6. The blood pressure monitor according to claim 1, wherein the result of the assessment relates to orthostatic dysregulation.

7. The blood pressure monitor according to claim 1, wherein the processor is configured to indicate to the subject to make a transition from the recumbent position to the upright position after finishing calculation of the first blood pressure information.

8. A method of controlling a blood pressure monitor, the method comprising:

controlling a cuff pressure, which is an internal pressure of a cuff attached to a measurement site of a subject;

extracting a pulse wave signal from the measurement site as the cuff pressure is varied;

calculating blood pressure information of the subject based on a cuff pressure signal representing the cuff pressure and the extracted pulse wave signal superimposed on the cuff pressure signal, the calculation including calculating first blood pressure information of the subject who has maintained a recumbent position for a prescribed time period, and the controlling including maintaining the cuff pressure at a first pressure lower by a prescribed value than a systolic blood pressure included in the first blood pressure information;

determining whether an amplitude of the pulse wave signal of the subject is equal to or greater than a threshold value when the cuff pressure is maintained at the first pressure and the subject is in an upright position;

assessing an autonomic nerve function of the subject based on a result of the determination; and outputting a result of the assessment, wherein the result indicates suspected dysfunction of the autonomic nerve function if the amplitude of the pulse wave signal is less than the threshold value.

9. The method according to claim 8, wherein the controlling of the cuff pressure includes controlling the cuff pressure to be lowered from the first pressure when the amplitude of the pulse wave signal of the subject is smaller than the threshold value, the calculation of the blood pressure information includes calculating second blood pressure information of the subject during a process of lowering the cuff pressure from the first pressure, and the assessment of the autonomic nerve function includes assessing the autonomic nerve function of the subject further based on the first blood pressure information and the second blood pressure information.

10. The method according to claim 9, wherein the assessment of the autonomic nerve function includes assessing the autonomic nerve function of the subject based on a difference between a pulse rate included in the first blood pressure information and a pulse rate included in the second blood pressure information.

11. The method according to claim 9, wherein the assessment of the autonomic nerve function includes assessing the autonomic nerve function of the subject based on a difference between a pulse pressure included in the first blood pressure information and a pulse pressure included in the second blood pressure information.

12. The method according to claim 9, wherein the controlling the cuff pressure includes controlling the cuff pressure to increase after the second blood pressure information is calculated, wherein the method further comprises:

determining the cuff pressure at which the amplitude of the pulse wave signal of the subject is smaller than the threshold value during a process of increasing the cuff pressure; and calculating time elapsed between a first time when the amplitude of the pulse wave signal of the subject is determined to be smaller than the threshold value and a second time when a difference between a maximum value and a minimum value of a calculated systolic blood pressure corresponding to the cuff pressure during a prescribed period is equal to or smaller than a threshold pressure value, wherein the assessment of the autonomic nerve function includes assessing the autonomic nerve function of the subject further based on the elapsed time.

13. The method according to claim 8, wherein the result of the assessment relates to orthostatic dysregulation.

14. The method according to claim 8, further comprising indicating to the subject to make a transition from the recumbent position to the upright position after finishing calculation of the first blood pressure information.

* * * * *